United States Patent [19]

Reimer, deceased

[11] Patent Number: Plant 6,245

[45] Date of Patent: Aug. 9, 1988

[54] REIMER CULTIVAR PEAR TREE

[75] Inventor: Frank Reimer, deceased, late of Inglewood, Calif., by Matthew G. McCoy, administrator

[73] Assignee: The State of Oregon/Oregon State University, Corvallis, Oreg.

[21] Appl. No.: 856,153

[22] Filed: Apr. 25, 1986

[51] Int. Cl.[4] ..... A01H 5/03

[52] U.S. Cl. ..... Plt./36

[58] Field of Search ..... Plt./36

*Primary Examiner*—Robert E. Bagwill

*Attorney, Agent, or Firm*—Chernoff, Vilhauer, McClung & Stenzel

[57] ABSTRACT

A pear tree, which is a planned cross between Max Red Bartlett and Comice is characterized by its heavy crop of large red-skinned fruit of excellent dessert quality which have long storage life.

4 Drawing Sheets

BACKGROUND AND SUMMARY OF THE INVENTION

This invention relates to a new and distinct variety of pear tree, which was the result of a planned cross between the Comice (unpatented and the pistillate parent), and the Max Red Bartlett (U.S. Plant Pat. No. 741).

The new pear variety originated at the Southern Oregon Agricultural Experiment Station located near Medford, Oreg. from controlled crosses made by the inventor in or about the year 1940. The subject variety has several qualities which now are in demand in the pear industry, such as the ability to crop heavily and regularly, provide large, attractive, red-skinned fruit of top dessert quality, and produce fruit that possess long storage life for fresh market and gift market needs. The subject plant bears large-fruited red pears which are particularly suited for the holiday and late winter markets. Its fruit has excellent dessert quality and it possesses an attractive, bright, glossy red blush appearance when displayed on shelves and in gift boxes. It has a storage life of up to eight (8) months when properly stored.

The subject variety has been asexually reproduced and subsequent second and third generations of trees have been tested thoroughly and evaluated at the Southern Oregon Agricultural Experiment Station over the past twenty-eight (28) years.

GENERAL DETAILED DESCRIPTION OF THE INVENTION

Figure 1:
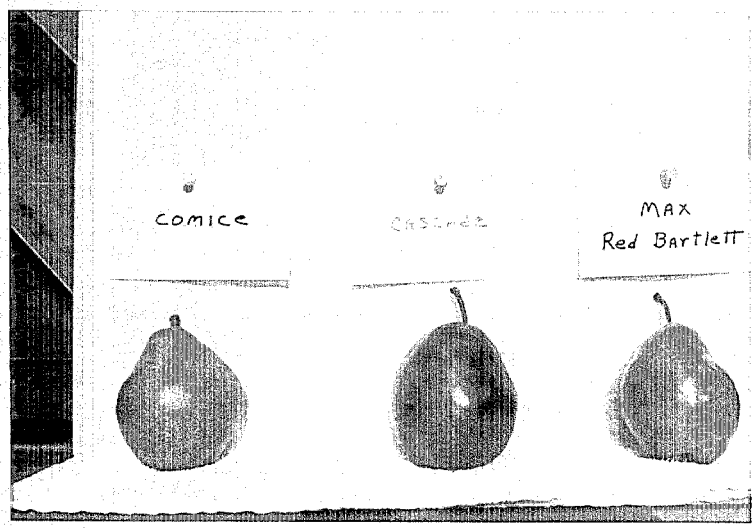
FIGS. 1, 2, 3 and 4 show the fruit of the subject variety in comparison with the fruit of its parents.
Figure 2:
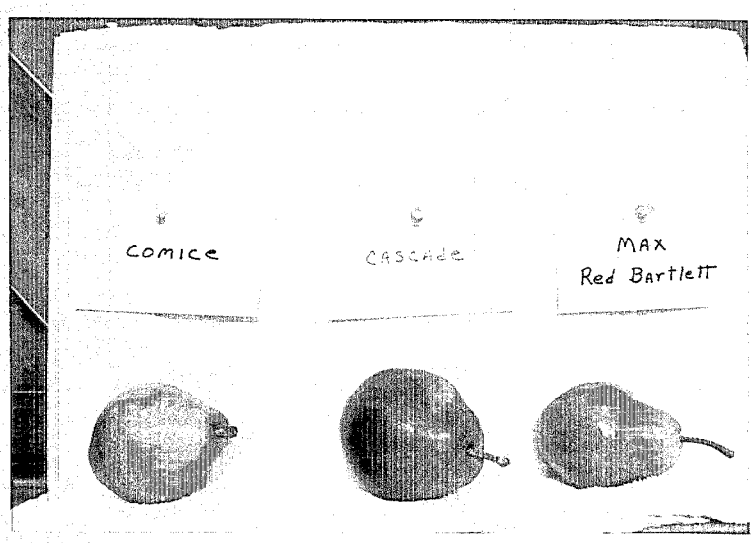
Figure 3:
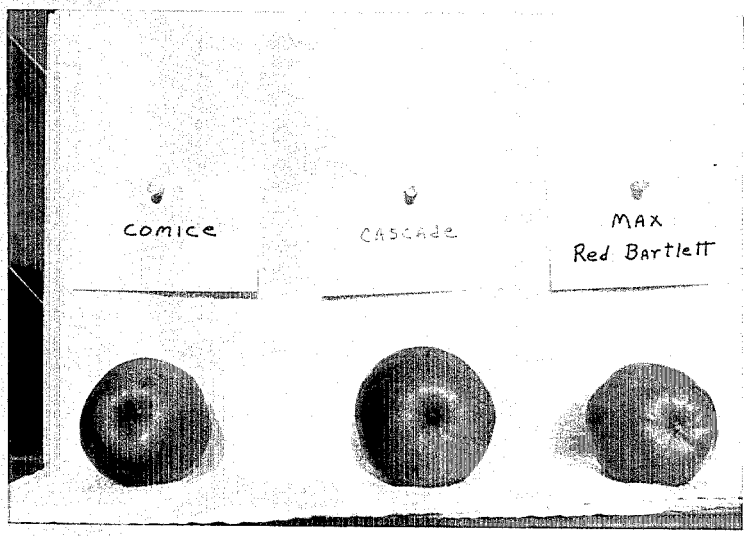
Figure 4:
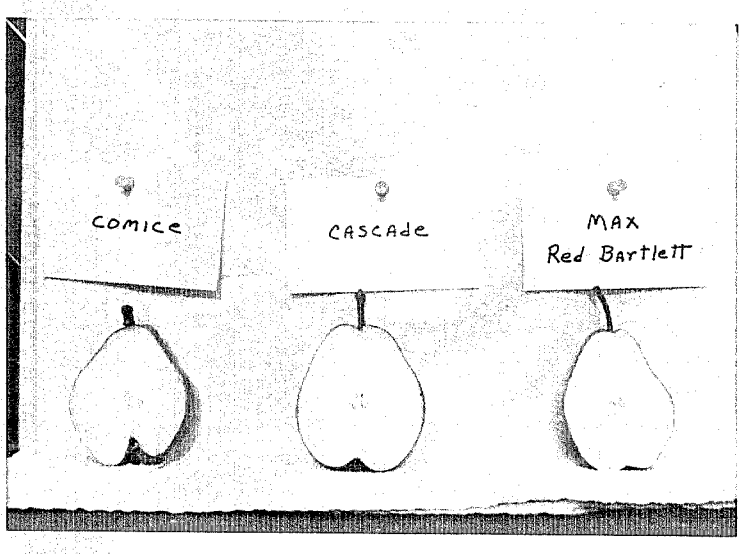
Figure 5:
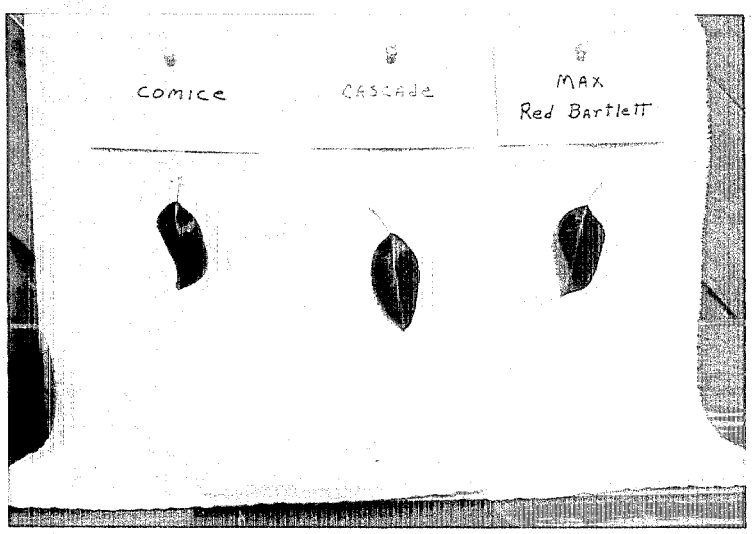
FIG. 5 shows a typical leaf of the subject variety in comparison with the leaves of its parents.
Figure 6:
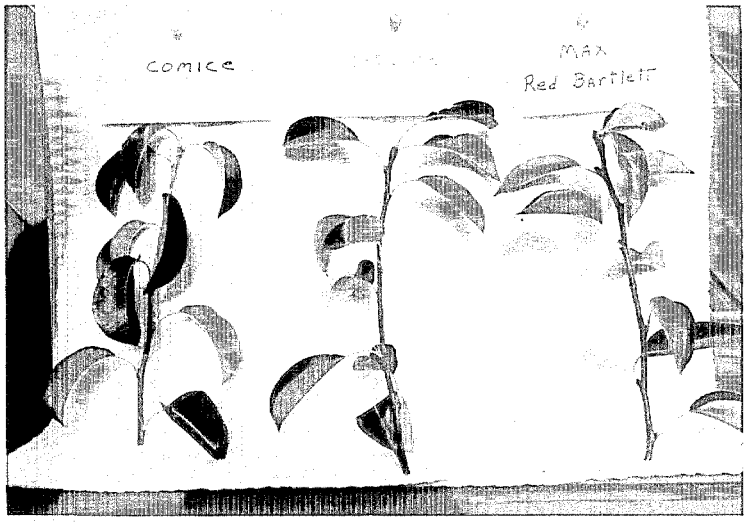
FIG. 6 shows a twig of the subject variety in comparison with the twigs of its parents.
Figure 7:
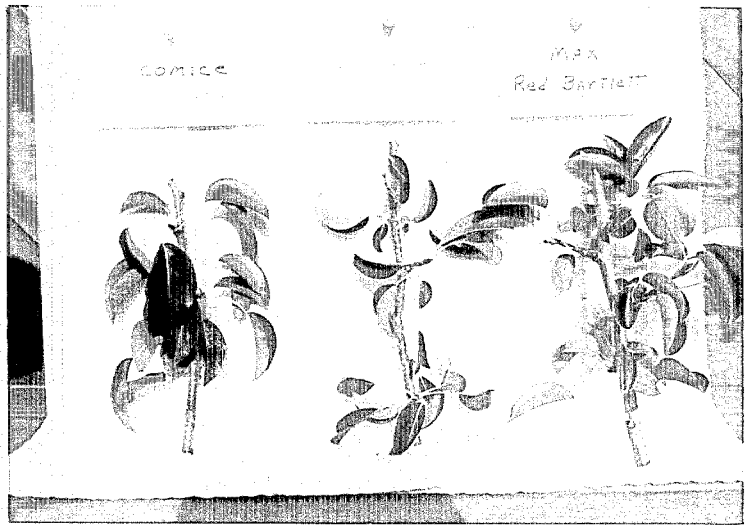
FIG. 7 shows spur growth of the subject variety in comparison with the spur growth of its parents.

Trees of the subject variety growing on *Pyrus communis* seedling rootstocks are vigorous and upright in growth. Cropping is heavy and regular in mature trees. In comparison with both of its parents, the subject variety is distinctively characterized as follows:

(1) The bloom period of the subject variety follows the bloom period of Max Red Bartlett by several days but is slightly ahead of the bloom period of Comice, overlapping both of its parents. It is not self-fruitful but can effectively be cross-pollinated with pollen from either of its parents.

(2) Fruit maturity and harvest dates of the subject variety follow those of Max Red Bartlett by about 10 days. Its fruit should be harvested about 10 days ahead of its other parent, the Comice variety.

(3) Its storage life exceeds that of Max Red Bartlett by at least four months and Comice by two months.

(4) Few stone grit cells have been observed in the fruits of the subject variety like the flesh of its parents.

(5) Its fruit shape is intermediate between Max Red Bartlett and Comice, being plump in the distal portion with a recessed calyx, while maintaining a distinct shoulder and moderately tapered neck.

(6) Cropping is heavier in the subject variety than either Max Red Bartlett or the red sport of Comice. (See the following table.)

PRODUCTION OF REIMER CULTIVAR PEAR TREES COMPARED TO TWO OTHER RED PEARS CULTIVARS AT MEDFORD, OREGON

| | | Production per tree (lbs.) | |
|---|---|---|---|
| | Date: | 1982 | 1983 |
| Cultivar | Age of tree: | 5 yr. | 6 yr. |
| Reimer | | 5.5 | 30.6 |
| Red Sensation Bartlett | | 3.5 | 27.5 |
| Red Comice | | 0.8 | 7.0 |

| | | Production in tons/acre | |
|---|---|---|---|
| Cultivar | Planting density (tr/ac) | 1982 | 1983 |
| Reimer | 360* | 1.0 | 5.5 |
| | 720** | 2.0 | 11.0 |
| Red Sensation Bartlett | 360* | 0.6 | 5.0 |
| | 720** | 1.2 | 10.0 |
| Red Comice | 360* | 0.1 | 1.3 |
| | 720** | 0.3 | 2.5 |

*On three different rootstocks through all cultivars: OPR 1, OH × F 97, P. Calleryana seedling planted at 10 × 12.5 feet.

**On five different rootstocks: OH × F 51, OH × F 9, Provence Quince, Quince "A", and self-rooted Bartlett planted at 5 × 12.5 feet.

Growth habit is similar to its pollen parent the Max Red Bartlett. Leaves, twigs and spur growth are similar to both of its parents, except for the noticeably darker bark and the conspicuous, large, raised tan-colored lenticels on second year twigs. Both of its parent possess smooth, less-conspicuous lenticels on twigs of the same age.

DETAILED DESCRIPTION OF VEGETATIVE CHARACTERISTICS

The following detailed description of this new pear variety is based on observations made of a thirteen year-old second generation tree growing at the Southern Oregon Agricultural Experiment Station site near Medford, Oreg. All major colors referred to being by reference to the *Munsell Cascade Color Chart* except where common terms of color definition are employed. The pear tree may vary in slight detail due to climatic and soil conditions if it is grown in another region.

Tree:
- *Size.*—Medium to large.
- *Vigor.*—Vigorous.
- *Form.*—Upright, tall, round-topped, drooping.
- *Growth.*—Moderate.
- *Hardiness.*—Hardy.
- *Production.*—Very productive.
- *Bearing.*—Regular in mature trees, some alternate bearing on young trees.
- *Compatability.*—Compatible with all commercially used pear rootstocks, including quince.
- *Susceptibility.*—Susceptible to normal pear pests and diseases.
- *Adaptability.*—Dependent on rootstocks used.

Trunk:
- *Form.*—Straight, stout.
- *Size.*—Medium.
- *Texture.*—Shaggy.

Branches:
- *Main branches.*—Upright, straight, slender, strong.
- *Lateral branches.*—Slender, long-jointed, glabrous, straight, medium smooth, covered with gray scarf skin over reddish brown.
- *Branchlets.*—Slender, long with long internodes, glabrous, reddish.
- *Lenticels.*—Many, raised, tan, very conspicuous, large.

Leaves:
- *Size.*—Medium, average length 3" to 3½" average width 1½" to ¾".
- *Form.*—Broad-ovate.
- *Apex.*—Taper-pointed to abruptly pointed.
- *Thickness.*—Medium thick.
- *Pubescence.*—None.
- *Texture.*—Smooth, leathery.
- *Margin.*—Crevate-serrate, small teeth, slight fold upward.
- *Petiole.*—Slender, average length 1½ inch.
- *Color.*—Topside medium-green (22-12), underside light-green (22-10).

Leaf-buds:
- *Form.*—Small, short, obtuse, free.

Leaf-scars: Inconspicuous.

Flowers:
- *Blooming period.*—In Medford, Oreg. about Apr. 5 to Apr. 15.
- *Size.*—Large" average diameter 1⅜" to 1½".
- *Color.*—White.

Petals:
- *Shape.*—Obovate, broad.
- *Color.*—White with pink tips when newly opened.
- *Fertility.*—Crops best with cross-pollination.
- *Pedicels.*—Pubescent, reddish, thick, ½" to ¾" long.

Flower buds:
- *SiZe.*—Medium.
- *Shape.*—Conical, plump, free.

Fruit:
- *Date of first picking.*—In Medford, Oreg. about September 1.
- *Date of last picking.*—In Medford, Oreg. about September 15.
- *Retention.*—Hangs well.
- *Size.*—Very large, uniform, average length 3¾" to 4", average width 3¼" to 3½".
- *Form.*—Pyriform, short neck, distinct, obtuse, regular surface outline, equal sides.
- *Stem.*—Woody, very thick, average length ¾" to 1".
- *Cavity.*—Obtuse, shallow, smooth, uniform, radiating red streaks.
- *Calyx.*—Open, large.
- *Lobes.*—Closed, medium length, medium breadth, acute, separated at base, slightly fleshy at base.
- *Basin.*—Large, shallow, obtuse, smooth, symmetrical, regular.

Skin:
- *Texture.*—Smooth, thick, tough.
- *Color.*—Bright-red (37-14), greenish yellow color (24-8), smooth basin, russet free.
- *Dots.*—Inconspicuous, small.

Flesh:
- *Color.*—White.
- *Texture.*—Fine grained, tender, juicy, buttery, free from grit-cells.
- *Flavor.*—Sweet, rich aromatic.
- *Eating quality.*—Best, very delicious.
- *Core.*—Large, closed, bluntly pointed at upper end and long pointed at lower end.
- *Core-lines.*—Clasping, indistinct, wide to ¼", obovate.
- *Core cavity.*—tufted.
- *Calyx-tube.*—Funnel-shaped, open limb, cylinder often closed.

Seed:
- *Seed.*—Large.
- *Shape.*—Wide, long, plump, accuminate, point not tufted, point very acute.
- *Color.*—Dark-brown (28-14).

What is claimed is:

1. A new and distinct variety of pear tree substantially as described and illustrated, obtained as a seedling from a seed parent Max Red Bartlett (U.S. Plant Pat. No. 741) and a pollen parent Comice, characterized by its ability to produce a heavy crop of large, attractive, red-skinned fruit of excellent dessert quality which have long storage life.

* * * * *

UNITED STATES PATENT AND TRADEMARK OFFICE

CERTIFICATE OF CORRECTION

PATENT NO. : Plant 6,245

DATED : August 9, 1988

INVENTOR(S) : Frank Reimer

It is certified that error appears in the above-identified patent and that said Letters Patent is hereby corrected as shown below:

Col. 4, line 9 Change "siZe" to --size--

Col. 4, line 43 Change "1/4" to --1-1/4--

Signed and Sealed this

Twenty-seventh Day of March, 1990

*Attest:*

JEFFREY M. SAMUELS

*Attesting Officer*

*Acting Commissioner of Patents and Trademarks*